US008343155B2

(12) United States Patent
Fisher et al.

(10) Patent No.: US 8,343,155 B2
(45) Date of Patent: Jan. 1, 2013

(54) CABLE BUTTON

(75) Inventors: Larabeth Gladys Fisher, Warsaw, IN (US); Michael Joseph LaLonde, Warsaw, IN (US); Michael Kent Keith, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 1236 days.

(21) Appl. No.: 12/120,708

(22) Filed: May 15, 2008

(65) Prior Publication Data

US 2009/0287215 A1    Nov. 19, 2009

(51) Int. Cl.
*A61B 17/56* (2006.01)
*A61B 17/58* (2006.01)
*A61B 17/82* (2006.01)
*A61F 2/30* (2006.01)

(52) U.S. Cl. ........................................................ 606/74
(58) Field of Classification Search .................... 606/74, 606/300, 232, 281, 283, 284, 286
See application file for complete search history.

(56) References Cited

U.S. PATENT DOCUMENTS

| 5,190,545 | A   |   | 3/1993  | Corsi et al.     |        |
|-----------|-----|---|---------|------------------|--------|
| 5,702,399 | A   |   | 12/1997 | Kilpela et al.   |        |
| 5,810,824 | A   | * | 9/1998  | Chan             | 606/70 |
| 6,960,213 | B2  | * | 11/2005 | Chervitz et al.  | 606/74 |
| 7,250,054 | B2  | * | 7/2007  | Allen et al.     | 606/74 |

FOREIGN PATENT DOCUMENTS

WO    WO93/03681 A1    3/1993

OTHER PUBLICATIONS

Zimmer Product Brochure "Greater Trochanteric Reattachment" Cable-Ready Cable Grip System, 97-2232-13 20ML, 2001 Zimmer, Inc.
Zimmer Product Brochure "Comprehensive Cable Grip System" Cable-Ready Cable Grip System, 97-2232-201 20ML, 2001 Zimmer, Inc.
Webpage—www.pioneersurgical.com/products_ortho_zimmer_hexbtn.asp?menu=3,2,8 1/7/2008—Hex Button.
Webpage—www.pioneersurgical.com/products_ortho_zimmer_cabplate.asp?menu=3,2,7 1/7/2008—Cable Plate.
Webpage—www.pioneersurgical.com/products_ortho_zimmer_cerccab.asp?menu=3,2,6 1/7/2008—Cerclage Cable.
Webpage—www.pioneersurgical.com/products_ortho_zimmer_gtr.asp?menu=3,2,3 1/7/2008—Greater Trochanter Reattachment.

* cited by examiner

*Primary Examiner* — Anu Ramana
(74) *Attorney, Agent, or Firm* — Schwegman, Lundberg & Woessner, P.A.

(57) ABSTRACT

The present disclosure includes a method for reducing a bone fracture and an apparatus such as a cable button for use with a bone plate, the cable button including cable button threads, a plurality of cable button apertures, a hex socket, and a hex opening. The present disclosure also includes a method for reducing a bone fracture and an apparatus such as a cable button for use with a bone plate, the cable button including a plurality of legs, where a leg includes a protrusion, where the protrusion engages the bone plate, and the cable button defines at least one cable button aperture.

23 Claims, 5 Drawing Sheets

CABLE BUTTON

BACKGROUND

It is known to treat fractures in bones by reducing the bone fracture. A bone or trauma plate may be attached to the bone to assist the fracture in the healing process. Generally, reducing the fracture includes realigning and positioning the fractured portions of the bone to their original position or a similar stable position. In addition, fixing the fracture with a bone plate includes positioning the plate over the fractured area of the bone and securing the plate to the bone across the fracture. Bone plates are configured to hold the bone in place while the fracture heals. Additionally, the bone plate may also provide support and/or compression to the bone in order to compress the fracture. Typically, such bone plates include a plurality of holes therein. The holes are configured to receive screws which are inserted into the bone to secure the bone plate to the bone.

SUMMARY

The present disclosure provides, a cable button for use with a bone plate and a cerclage wire, the bone plate including at least one bone plate aperture including bone plate threads, the cable button comprising a body defining a longitudinal axis, the body defining cable button threads extending along a first portion of the body, the body defining a plurality of cable button apertures extending along a second portion of the body, whereby the cerclage wire is configured to pass through at least one of the plurality of cable button apertures.

Another embodiment of the present disclosure provides, a method of reducing a bone fracture in a bone, the method comprising the steps of providing a bone plate, a cable button, and a cerclage wire, the bone plate defining at least one bone plate aperture, the cable button defining at least one cable button aperture, securing the cable button to the bone plate, positioning the cerclage wire around the bone and the bone plate, guiding the cerclage wire through at least one of the cable button apertures, and securing the cerclage wire to the bone to compress the bone fracture.

Yet another embodiment of the present disclosure provides, a bone fracture reduction apparatus comprising a bone plate defining at least one bone plate aperture, a cable button configured to secure to the bone plate, the cable button defining a plurality of cable button apertures, and a cerclage wire at least partially located within at least one of the plurality of cable button apertures.

Yet another embodiment of the present disclosure provides, a bone fracture reduction apparatus comprising a bone plate defining at least one bone plate aperture, a cerclage wire configured to secure to the bone plate, and means for securing the cerclage wire to the bone plate.

BRIEF DESCRIPTION OF THE DRAWINGS

The above-mentioned and other features of this invention, and the manner of attaining them, will become more apparent and the invention itself will be better understood by reference to the following description of embodiments of the invention taken in conjunction with the accompanying drawings, wherein.

Figure 1:
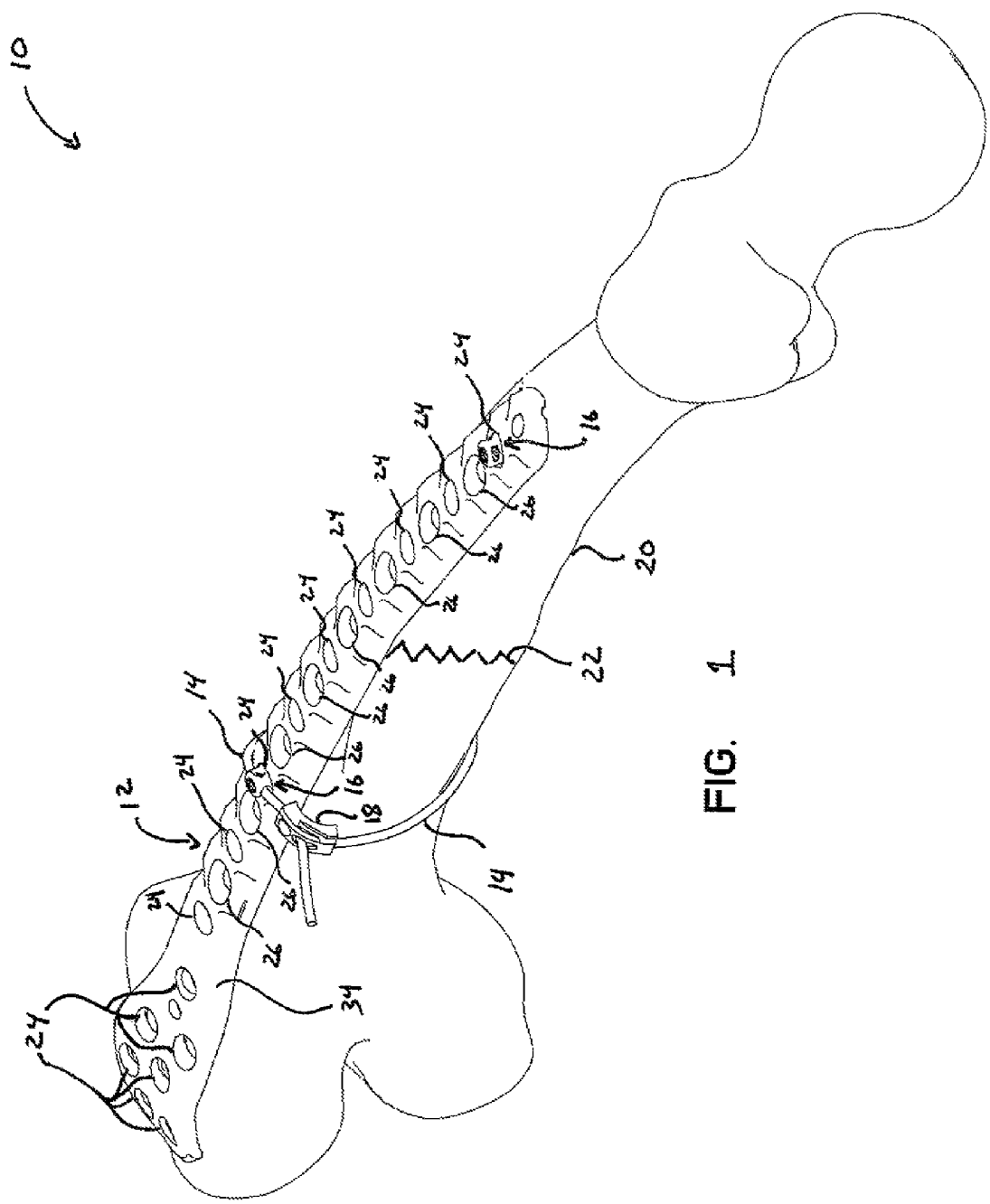
FIG. 1 is a perspective view of a bone having a bone fracture and a bone plate including a cerclage wire and a cable button according to the present disclosure.

Corresponding reference characters indicate corresponding parts throughout the several views. Although the drawings represent embodiments of the present invention, the drawings are not necessarily to scale and certain features may be exaggerated in order to better illustrate and explain the present invention.

DETAILED DESCRIPTION OF THE EXEMPLARY EMBODIMENTS

The embodiments disclosed below are not intended to be exhaustive or limit the invention to the precise forms disclosed in the following detailed description. Rather, the embodiments are chosen and described so that others skilled in the art may utilize their teachings.

Referring to FIG. 1, bone plate assembly 10 is shown. Bone plate assembly 10 includes bone plate 12, cerclage wire 14, and cable button 16. Bone plate assembly 10 optionally includes surgical connector 18. Bone plate 12 is secured to bone 20 by cerclage wire 14, and cable button 16. Cable button 16 is secured to bone plate 12. Bone plate assembly 10 is secured to bone 20 to hold bone fracture 22 or fragments of bone 20 in place until bone 20 heals.

Figure 2:
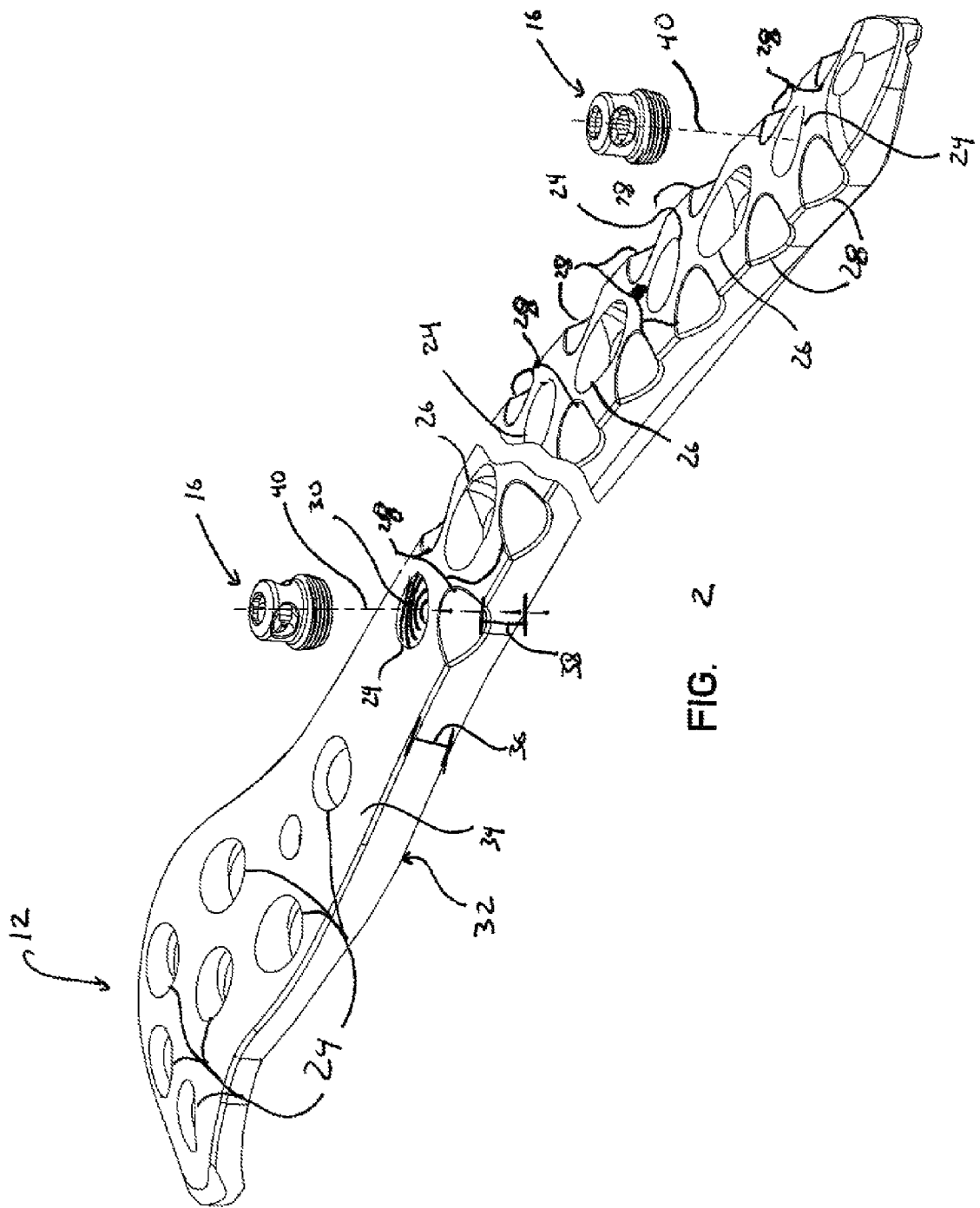
FIG. 2 is an exploded view showing another embodiment of bone plate and the cable button of FIG. 1.

Bone plate 12 is shown defining bone plate apertures 24 for receipt of cable buttons 16. Bone plate apertures 24 are illustrated as cylindrical, however, bone plate apertures 24 may include many different shapes such as conical, spherical, polygon, and elliptical. Spherical shaped bone screw apertures 26 are for receipt of spherical shaped bone screws (not shown). Scallops 28, illustrated as curved indentures defined by bone plate 12, are configured to form or contour bone plate 12. As illustrated in FIG. 2, bone plate 12 optionally defines threading 30 for cable buttons 16. Cable buttons 16 are secured, such as by threading 30, to bone plate 12 by bone plate apertures 24. Cerclage wire 14 is secured to bone plate 12 by use of cable buttons 16 as discussed in greater detail below. Optionally, surgical connector 18 is coupled to cerclage wire 14 to secure cerclage wire 14 about bone 20 in order to hold bone fracture 22 and/or fragments of bone 20 in place until bone heals.

Referring to FIG. 2, bone plate 12 and cable button 16 are shown as one embodiment in accordance with the present disclosure. Bone plate 12 includes bone contacting surface 32 and surface 34 opposite bone contacting surface 32. Bone plate 12 also defines bone plate height 36 as the distance between bone contacting surface 32 and opposite surface 34. As illustrated, bone contacting surface 32 and opposite surface 34 each have contour and are not substantially flat. Bone contacting surface 32 and opposite surface 34 are illustrated as non-parallel and are shown to have divergent surfaces. Bone plate height 36 varies. Bone plate 12 defines threading bone plate height 38 as the distance between bone contacting surface 32 and opposite surface 34 along threading axis 40.

As shown in FIG. 2, bone plate 12 defines bone plate apertures 24. Bone plate 12 also defines bone plate threading 30. While bone plate 12 is described and depicted herein as being secured to bone 20, bone plate 12 may be secured in other locations and to other types of bones in accordance with the teachings herein. For example, bone 20 illustrates a femur.

However, bone plate 12 may be secured to other bones 20 such as the tibia, pelvis, humerous, ulna, radius, tarsus, metatarsus, scapula, clavicle, fibula, talus, vertebral bodies and phalanges.

Bone plate 12 may be constructed of any biocompatible ceramic or metal including, but not limited to, a titanium alloy, cobalt, chromium, cobalt chromium molybdenum, porous tantalum, or a highly porous biomaterial. A highly porous biomaterial is useful as a bone substitute and is a cell and tissue receptive material. Bone plate 12 may take several forms such as a periarticular plate which is a plate surrounding a joint, or a non-contact bridging plate where spacers may be used to hold the non-contact bridging plate off of bone 20.

FIG. 2 also illustrates threading axis 40, also known as a locking hole axis. As illustrated by FIG. 2, cable button 16 threads into bone plate aperture 24 along threading axis 40. Threading axis 40 is shown as substantially perpendicular to bone plate 12. However, cable button 16 may be secured to bone plate 12 along other angles of threading axis 40 relative to bone plate 12, in accordance with the teachings herein. As previously described, cable button 16 is configured to secure cerclage wire 14 to bone 20 (FIG. 1), as well as bone plate 12.

Figure 3:
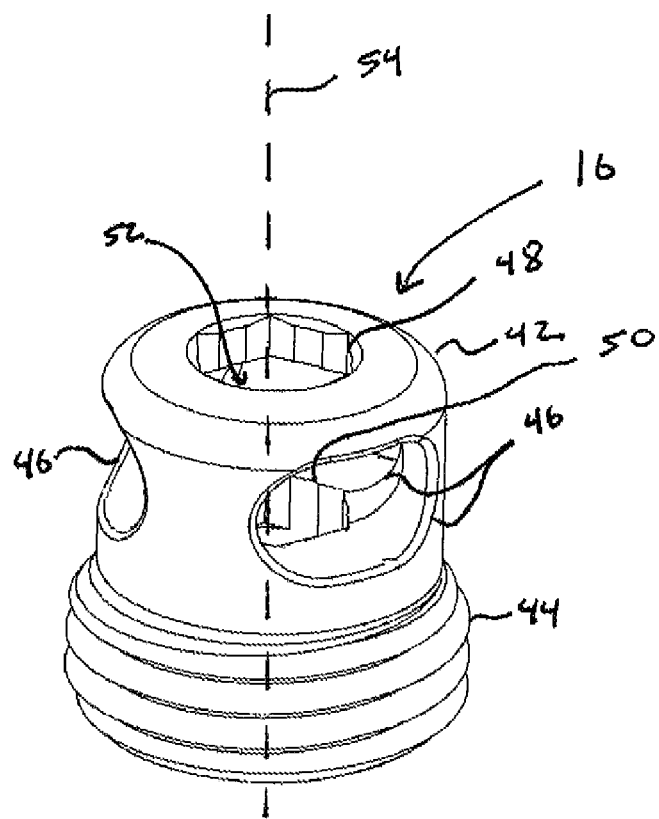
FIG. 3 is a perspective view of the cable button of FIG. 1.

Referring to FIG. 3, cable button 16 includes body 42 which defines cable button threading 44. Cable button 16 also defines cable apertures 46, cable button polygon opening 48, such as hex opening 48, cable button polygon socket 50, such as hex socket 50, as well as cable button cavity 52. As previously discussed, cable button threading 44 is configured to align with bone plate threading 30 (FIG. 2) as defined by bone plate 12 (FIG. 2). In this embodiment, cable button cavity 52 is in communication with cable apertures 46, cable button hex opening 48, and cable button hex socket 50. Cable apertures 46 are also configured to receive cerclage wire 14 as previously shown in FIG. 1.

A cable passer, as illustrated by the assignee of the present invention as Cable Ready Long Guided Tissue Regeneration (GTR) and incorporated herein by reference, is configured to pass cerclage wire 14 (FIG. 1) around bone 20 (FIG. 1). The cable passer is passed around bone 20. The cable passer defines a shaft configured to accept cerclage wire 14. Cerclage wire 14 is inserted into the shaft at an end of the cable passer. Cerclage wire 14 exits the shaft. The cable passer is withdrawn, leaving cerclage wire 14 around bone 20. Cerclage wire 14 is configured to pass through cable button 16 as discussed in greater detail below.

Three cable apertures 46 are shown in FIG. 3. However, there may be a plurality of cable apertures 46, such as one, two, three, four, five, six or more apertures. Cable button 16 defines more than two cable apertures 46 in order to provide a combination of passages for cerclage wire 14 (FIG. 1). Cerclage wire 14 may be passed through a plurality of cable apertures 46 and cable button cavity 52. Cable button 16 provides a plurality of passages for passing cerclage wire 14 through cable button 16 to provide a plurality of passage orientations relative to bone plate 12 (FIG. 1). As illustrated in FIG. 1, cable button 16 is threaded into bone plate aperture 24. The angular orientation of cable button 16 may define the angular orientation of a cerclage wire passage. As cable button 16 is threaded onto bone plate 12, annular orientation of cable button 16 defines angular orientation of the plurality of passages relative to bone plate 12. Therefore cerclage wire 14 may secure bone plate 12 to bone 20 (FIG. 1) in a plurality of potential positions.

Cable button 16 also defines cable button hex socket 50 and cable button hex opening 48. As previously described, cable button hex opening 48 is in communication with cable button cavity 52. Also, cable button cavity 52 is in communication with cable button hex socket 50. In one embodiment, cable button hex socket 50, cable button cavity 52, and cable button hex opening 48 are located along longitudinal axis 54. In another embodiment, longitudinal axis 54 substantially aligns with threading axis 40 (FIG. 2). Cable button hex socket 50 provides a hex shaped arrangement for a screw driver (not shown), such as a hex driver or Allen wrench. Cable button hex socket 50 causes cable button 16 to act similar to the head of a locking screw (not shown) for threading into bone plate aperture 24 (FIG. 2). Cable button hex opening 48 provides the driver access to cable button hex socket 50. Furthermore cable button hex opening 48 can engage the hex driver (not shown) to assist in screwing cable button 16 into or out of bone plate 12 (FIG. 2).

Figure 4:
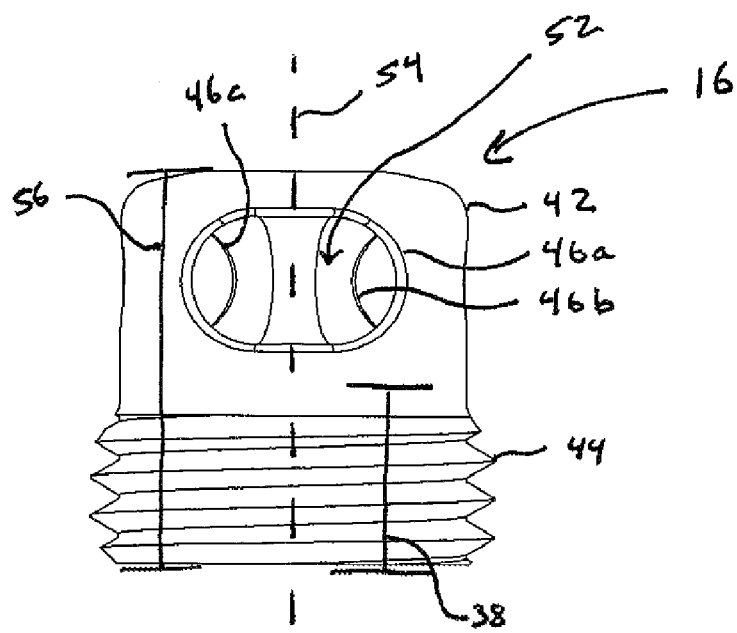
FIG. 4 is a front view of the cable button of FIG. 1.

Referring now to FIG. 4, cable button 16 also defines longitudinal axis 54. Cable button 16 also defines cable button height 56 along longitudinal axis 54. As illustrated, cable button height 56 is greater than threading bone plate height 38. As illustrated, threading bone plate height 38 substantially corresponds to the height of cable button threading 44. As also illustrated, cable apertures 46 are located within cable button height 56 but not within threading bone plate height 38. In one embodiment, cable apertures 46 are located substantially adjacent to threading bone plate height 38. In this embodiment, cerclage wire 14 (FIG. 1) could be guided though cable aperture 46, cable button 16 could be threaded down onto bone plate 12 such that cerclage wire 14 is secured to opposite surface 34 (FIG. 2).

First cable aperture 46a is shown to intersect, i.e. provide fluid communication, with cable button cavity 52. Cable button cavity 52 is also in communication with second and third cable apertures 46b and 46c. The combination of first cable aperture 46a and second cable aperture 46b provide a first cerclage wire passage. The combination of first cable aperture 46a and third cable aperture 46c provide a second cerclage wire passage. Furthermore, the combination of second and third cable apertures 46b and 46c provide a third cerclage wire passage.

Figure 5:
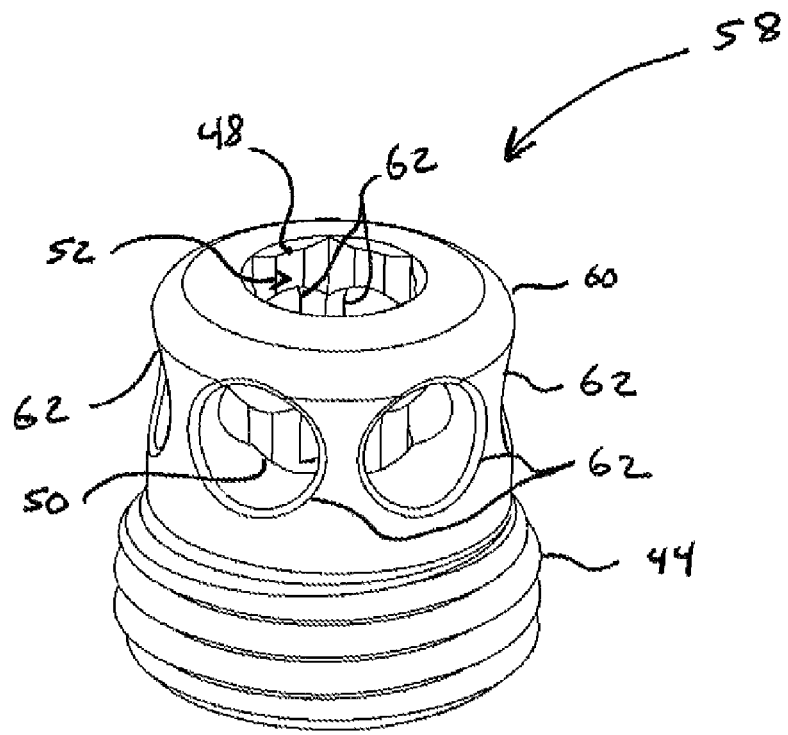
FIG. 5 is a perspective view of another embodiment of a cable button according to the present disclosure.
Figure 6:
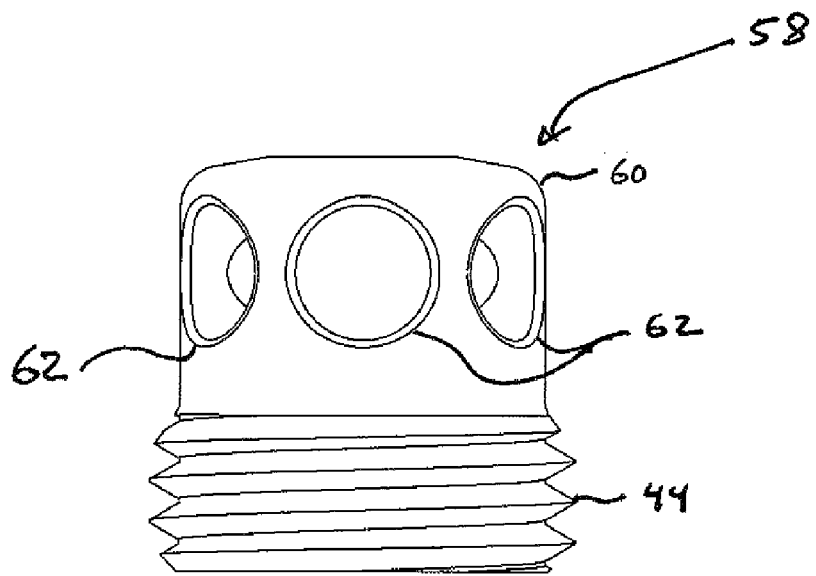
FIG. 6 is a front view of the cable button of FIG. 5.

As shown in FIG. 5, cable button 58 is shown as another embodiment of the present disclosure. Cable button 58 is substantially similar to cable button 16, except for the differences disclosed herein. Cable button 58 includes body 60 which defines cable apertures 62. Six cable apertures 62 provide several cerclage wire passages similar to cable button 16. As shown in FIG. 6 and similar to cable button 16, cable button 58 defines a plurality of cerclage wire passages. At least one cerclage wire passage is illustrated.

Figure 7:
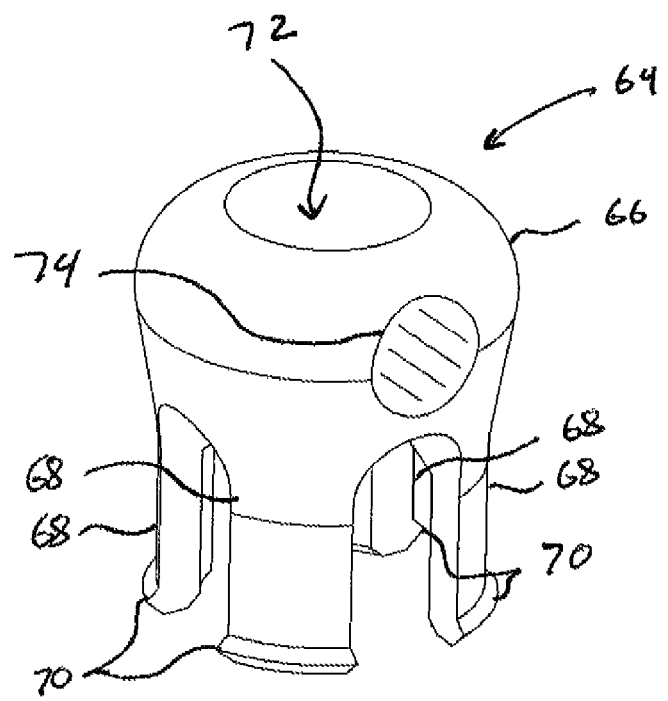
FIG. 7 is a perspective view of another embodiment of a cable button according to the present disclosure.

Referring now to FIG. 7, cable button 64 is shown as yet another embodiment of the present disclosure. Cable button 64 is substantially similar to cable button 16, except for the differences disclosed herein. Cable button 64 includes body 66 including legs 68 including protrusion 70. More specifically, protrusion 70 extends radially outward from leg 68. Body 66 also defines depression 72 and at least one cable aperture 74. Depression 72 is configured to assist in pressing body 66 into bone plate aperture 24 (FIG. 1).

Similar to previous embodiments of cable button 16 (FIG. 1), cable button 64 is secured to bone plate 12 (FIG. 1) through bone plate aperture 24 (FIG. 1). In one embodiment, bone plate 12 is not threaded. In this embodiment, cable button 64 does not thread into bone plate 12, but instead uses bias, lock, and catch mechanisms. Legs 68 and protrusion 70 are biased inwards when pressed through aperture 24 and are able to release and to catch bone contacting surface 32 (FIG. 2) of bone plate 12. In another embodiment, bone plate 12 defines threading 30 (FIG. 2). In this embodiment, cable button 64 may be positioned in the grooves defined by threading 30 in bone plate 12.

Figure 8:
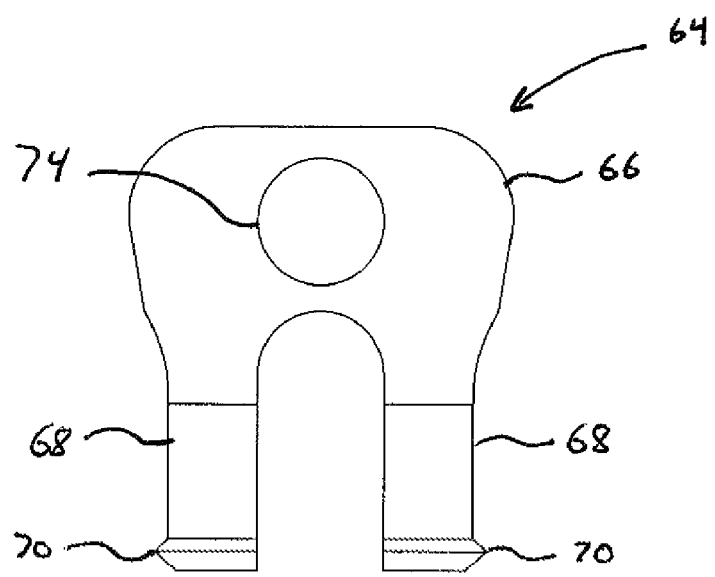
FIG. 8 is a front view of the cable button of FIG. 7.

As shown in FIG. 8, cable button 64 shows at least one cerclage wire passage. Cable button 64 is configured to secure to bone plate 12 such as by threading as previously discussed. The angular orientation of cable button 64 may define the angular orientation of a cerclage wire passage. As cable button 64 is threaded onto bone plate 12, annular orientation of cable button 64 defines angular orientation of the plurality of passages relative to bone plate 12. Therefore cerclage wire 14 may secure bone plate 12 to bone 20 (FIG. 1) in a plurality of potential positions. In an alternative embodiment, cable button 64 is configured to rotate cable aperture 74 while cable button 64 is secured to bone plate 12. Therefore cerclage wire 14 may secure bone plate 12 to bone 20 (FIG. 1) in a plurality of potential positions.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of reducing a bone fracture in a bone, comprising the steps of:
   providing a bone plate including a bone contacting surface and an opposing surface opposite the bone contacting surface, the bone plate defining a bone plate height between the bone contacting surface and the opposing surface, the bone plate including at least one threaded bone plate aperture extending from the bone contacting surface to the opposing surface;
   providing a cable button including a fastener portion and a head extending from the fastener portion, the fastener portion of the cable button including a fastener defining a thread, the fastener portion sized to be positioned within the threaded bone plate aperture, the fastener sized and shaped to secure the cable button to the bone plate so that the fastener resists movement of the cable button along a longitudinal axis of the cable button relative to the bone plate when the fastener portion of the cable button is positioned within the threaded bone plate aperture, the head of the cable button including a cable button aperture;
   positioning the cable button fastener portion into the threaded bone plate aperture and engaging the fastener to the bone plate, including threading the cable button into the threaded bone plate aperture, and thereby securing the cable button to the bone plate so that the fastener resists movement of the cable button along the longitudinal axis of the cable button relative to the bone plate;
   providing a cerclage wire, the cable button aperture sized to receive the cerclage wire;
   positioning the cerclage wire around the bone and atop the opposing surface of the bone plate;
   guiding the cerclage wire through the cable button aperture; and
   securing the cerclage wire to the bone to compress the bone fracture.

2. The method of reducing a bone fracture in a bone of claim 1, wherein the fastener portion of the cable button defines a fastener height, the fastener height being no more than the bone plate height, said securing the cable button to the bone plate including securing the cable button to the bone plate without extending the cable button beyond the bone contacting surface.

3. The method of reducing a bone fracture in a bone of claim 1, wherein the cable button aperture includes at least three spaced apertures extending from an exterior of the head of the cable button to an interior of the head of the cable button, a first of the at least three spaced apertures defining an entry for the cerclage wire, a second of the at least three spaced apertures defining an exit for the cerclage wire, and wherein guiding the cerclage wire through the cable button aperture includes guiding the cerclage wire through the entry and out the exit.

4. The method of reducing a bone fracture in a bone of claim 1, wherein positioning the cable button fastener portion into the bone plate aperture includes rotating the cable button to orient the cable button aperture relative to the bone plate.

5. The method of reducing a bone fracture in a bone of claim 1, wherein the cable button includes a driver recess for engaging a driver, and wherein threading the cable button into the threaded bone plate aperture includes engaging the driver with the driver recess and rotating the driver to thread the cable button into the threaded bone plate aperture.

6. A bone fracture reduction apparatus, comprising:
   a bone plate including a bone contacting surface and an opposing surface opposite said bone contacting surface, said bone plate defining a bone plate height between said bone contacting surface and said opposing surface, said bone plate including at least one threaded bone plate aperture extending from the bone contacting surface to the opposing surface;
   a cable button including a body, the body configured as an integral unit including a fastener portion and a head extending from said fastener portion, said fastener portion of said cable button including a fastener defining a thread sized to threadingly engage said threaded bone plate aperture to secure said cable button to said bone plate, said fastener portion sized to be positioned within said threaded bone plate aperture, said fastener sized and shaped to secure said cable button to said bone plate when said fastener portion base of said cable button is positioned within said threaded bone plate aperture so that said fastener resists movement of said cable button along a longitudinal axis of said cable button relative to said bone plate, said head of said cable button including a cable button aperture, said cable button sized and shaped so that said head of said cable button is situated above said opposing surface of said bone plate when said fastener secures said cable button to said bone plate whereby when said cable button is secured to said bone plate a cerclage wire positioned atop the opposing surface of the bone plate can be positioned through said cable button aperture of said cable button to retain the cerclage wire in said cable button aperture.

7. The bone fracture reduction apparatus of claim 6, wherein said fastener portion of said cable button defines a fastener height, said fastener height being no more than said bone plate height so that said cable button can fully engage said bone plate without extending beyond said bone contacting surface.

8. The bone fracture reduction apparatus of claim 6, wherein said cable button aperture comprises at least three spaced apertures extending from an exterior of said head of said cable button to an interior of said head of said cable button, a first of said at least three spaced apertures defining an entry for the cerclage wire, a second of said at least three spaced apertures defining an exit for the cerclage wire.

9. The bone fracture reduction apparatus of claim 6, wherein said cable button is rotatable relative to said bone plate when said cable button is secured to said bone plate so that rotation of said cable button orients said cable button aperture relative to said bone plate.

10. The bone fracture reduction apparatus of claim 6, wherein said cable button includes a driver recess for engaging a driver.

11. A bone fracture reduction apparatus, comprising:
a bone plate including a bone contacting surface and an opposing surface opposite said bone contacting surface, said bone plate defining a bone plate height between said bone contacting surface and said opposing surface, said bone plate including at least one threaded bone plate aperture extending from the bone contacting surface to the opposing surface; and
a cable button including a body, the body configured as an integral unit including a fastener portion and a head extending from said fastener portion, said fastener portion of said cable button including a fastener defining a thread sized to threadingly engage said threaded bone plate aperture to secure said cable button to said bone plate, said fastener portion sized to be positioned within said threaded bone plate aperture, said fastener sized and shaped to secure said cable button to said bone plate when said fastener portion of said cable button is positioned within said threaded bone plate aperture, said cable button comprising at least three spaced apertures sized to receive a cerclage wire, said at least three spaced apertures extending from an exterior of said head of said cable button to an interior of said head of said cable button, a first of said at least three spaced apertures defining an entry for the cerclage wire, a second of said at least three spaced apertures defining an exit for the cerclage wire.

12. The bone fracture reduction apparatus of claim 11, wherein said fastener is sized and shaped to secure the cable button to the bone plate so that said fastener resists movement of said cable button along a longitudinal axis of said cable button relative to said bone plate.

13. The bone fracture reduction apparatus of claim 11, wherein said cable button is sized and shaped so that said at least three spaced apertures of said cable button are situated above said opposing surface of said bone plate when said fastener secures said cable button to said bone plate whereby when said cable button is secured to said bone plate and the cerclage wire is positioned atop the bone plate, the cerclage wire can be positioned through a pair of said at least three spaced apertures of said cable button to retain said cerclage wire.

14. The bone fracture reduction apparatus of claim 11, wherein said fastener portion of said cable button defines a fastener height, said fastener height being no more than said bone plate height so that said cable button can fully engage said bone plate without extending beyond said bone contacting surface.

15. The bone fracture reduction apparatus of claim 11, wherein said cable button is rotatable relative to said bone plate when said cable button is secured to said bone plate so that rotation of said cable button orients said at least three spaced apertures of said cable button relative to said bone plate.

16. The bone fracture reduction apparatus of claim 11, wherein said cable button includes a driver recess for engaging a driver.

17. A bone fracture reduction apparatus, comprising:
a bone plate including a bone contacting surface and an opposing surface opposite said bone contacting surface, said bone plate defining a bone plate height between said bone contacting surface and said opposing surface, said bone plate including at least one bone plate aperture extending from the bone contacting surface to the opposing surface; and
a cable button including a body, the body configured as an integral unit including a fastener portion and a head extending from said fastener portion, said fastener portion of said cable button including a fastener comprising a protrusion extending radially outwardly from an exterior surface of said fastener portion, said fastener portion sized to be positioned within said bone plate aperture, said fastener sized and shaped to secure said cable button to said bone plate when said protrusion engages said bone contacting surface when said cable button is positioned within said bone plate aperture so that said fastener resists movement of said cable button along a longitudinal axis of said cable button relative to said bone plate, said head of said cable button including a cable button aperture, said cable button sized and shaped so that said head of said cable button is situated above said opposing surface of said bone plate when said fastener secures said cable button to said bone plate whereby when said cable button is secured to said bone plate a cerclage wire positioned atop the opposing surface of the bone plate can be positioned through said cable button aperture of said cable button to retain the cerclage wire in said cable button aperture.

18. The bone fracture reduction apparatus of claim 17, wherein said protrusion extends from a terminal end of said fastener portion of said cable button.

19. The bone fracture reduction apparatus of claim 17, wherein said fastener portion comprises a plurality of legs, said legs configured to be biased in a direction toward the interior surface of said fastener portion when said fastener portion is positioned within said bone plate aperture, said legs configured to return to an unbiased position after said legs extend beyond said bone plate aperture to said bone contacting surface of said bone plate so that said legs engage said bone contacting surface of said bone plate.

20. The bone fracture reduction apparatus of claim 17, wherein said cable button aperture comprises at least three spaced apertures extending from an exterior of said head of said cable button to an interior of said head of said cable button, a first of said at least three spaced apertures defining an entry for the cerclage wire, a second of said at least three spaced apertures defining an exit for the cerclage wire.

21. The bone fracture reduction apparatus of claim 20, wherein said cable button is rotatable relative to said bone plate when said cable button is secured to said bone plate so that rotation of said cable button orients said at least three spaced apertures of said cable button relative to said bone plate.

22. The bone fracture reduction apparatus of claim 17, wherein said cable button includes a driver recess for engaging a driver.

23. The bone fracture reduction apparatus of claim 17, wherein said fastener portion of said cable button defines a fastener height, said fastener height being no more than said bone plate height so that said cable button can fully engage said bone plate without extending beyond said bone contacting surface.

* * * * *